United States Patent
Kanazirev

(10) Patent No.: US 6,632,766 B2
(45) Date of Patent: Oct. 14, 2003

(54) COMPOSITE ADSORBENTS FOR PURIFYING HYDROCARBON STREAMS

(75) Inventor: Vladislav I. Kanazirev, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 271 days.

(21) Appl. No.: 09/733,693

(22) Filed: Dec. 8, 2000

(65) Prior Publication Data

US 2002/0147377 A1 Oct. 10, 2002

(51) Int. Cl.[7] .................. B01J 29/06; B01J 29/08
(52) U.S. Cl. ............... 502/64; 502/79; 502/400; 502/411
(58) Field of Search .................. 502/64, 79, 400, 502/411

(56) References Cited

U.S. PATENT DOCUMENTS

| | | | |
|---|---|---|---|
| 4,069,172 A | * 1/1978 | Kanaoka et al. | 502/68 |
| 4,376,103 A | * 3/1983 | Bertolacini et al. | 423/244.11 |
| 4,481,104 A | * 11/1984 | Walsh | 208/120.15 |
| 4,686,198 A | 8/1987 | Bush et al. | 502/25 |
| 4,717,483 A | 1/1988 | Bush et al. | 210/681 |
| 4,751,211 A | 6/1988 | Fleming | 502/64 |
| 4,762,537 A | 8/1988 | Fleming et al. | 55/71 |
| 4,808,742 A | 2/1989 | Fleming | 558/150 |
| 5,068,483 A | * 11/1991 | Barthomeuf et al. | 585/467 |
| 5,194,244 A | * 3/1993 | Brownscombe et al. | 423/700 |
| 5,672,799 A | * 9/1997 | Perego et al. | 585/467 |
| 6,013,600 A | * 1/2000 | Kanazirev | 502/415 |
| 6,090,738 A | * 7/2000 | Choudary et al. | 502/62 |
| 6,423,658 B1 | * 7/2002 | Thonnelier et al. | 502/64 |

FOREIGN PATENT DOCUMENTS

| | | | |
|---|---|---|---|
| JP | 7-48319 | * | 2/1995 |
| JP | 9-59204 | * | 3/1997 |

* cited by examiner

*Primary Examiner*—Tom Dunn
*Assistant Examiner*—Christina Ildebrando
(74) *Attorney, Agent, or Firm*—John G. Tolomei; Frank S. Molinaro

(57) ABSTRACT

Applicant has developed an improved adsorbent useful in removing contaminants from various hydrocarbon streams. The adsorbent contains a zeolite, an alumina and a metal component. The metal component (Madd) is present in an amount at least 10 mole % the stoichiometric amount of metal (M) (expressed as the oxide) needed to balance the negative charge of the zeolite lattice. In a specific application an adsorbent comprising zeolite X, alumina and sodium is used to purify an ethylene stream in order to remove $CO_2$, $H_2S$, methanol, and other S— and O— containing compounds.

16 Claims, No Drawings

COMPOSITE ADSORBENTS FOR PURIFYING HYDROCARBON STREAMS

FIELD OF THE INVENTION

This application relates to an adsorbent which comprises a zeolite, an alumina component and a metal component e.g. sodium in an amount at least 10% of the zeolite's ion exchange capacity. This new adsorbent is used to remove contaminants from hydrocarbon streams, e.g. removing $CO_2$, $CO_3$, $H_2S$, $AsH_3$, methanol, mercaptans and other S- or O-containing organic compounds from ethylene, propylene, $C_3$–$C_4$ hydrocarbon products and other lights hydrocarbon streams.

BACKGROUND OF THE INVENTION

Solid adsorbents are commonly used to remove contaminants from hydrocarbon streams such as olefins, natural gas and light hydrocarbon fractions. Since these streams can contain different contaminants, more than one adsorbent or adsorbent bed are needed to sufficiently purify the stream so that it can be used in the desired process. Contaminants which can be present in these streams include $H_2O$, CO, $O_2$, $CO_2$, COS, $H_2S$, $NH_3$, $AsH_3$, $PH_3$, Hg, methanol, mercaptans and other S- or O-containing organic compounds.

However, while various adsorbents can remove one or more contaminant, they can also remove and/or promote reactions of the desired hydrocarbon. For example, faujasite type zeolites, e.g. zeolite 13X, are good adsorbents for sulfur and oxygenate compounds but they are also good adsorbents for olefins which results in high temperature rise that can cause run-away reactions. Additionally, owing to the zeolite's residual surface reactivity reactions such as oligomerization and polymerization can occur during regeneration. This leads to fouling and performance deterioration.

In attempts to remedy this problem, there are reports in the art where zeolites have been mixed with alumina. U.S. Pat. No. 4,762,537 discloses the use of an adsorbent comprising zeolite Y and alumina to remove HCl from a hydrogen stream. In U.S. Pat. Nos. 4,686,198 and 4,717,483 it is disclosed that a mixture of alumina and sodium Y zeolite can remove ammonia sulfides and organic impurities from waste water. The sodium Y zeolite contains at least 12.7 wt. % $Na_2O$. The same adsorbent is also used to reduce the acidity and moisture content of used organophosphate functional fluids, see U.S. Pat. No. 4,751,211. The use of alumina with alkali or alkaline earth metal for removing HCl and other contaminants is disclosed in U.S. Pat. No. 6,013,600.

Applicant has developed an improved adsorbent which can remove multiple contaminants from various hydrocarbon streams. Surprisingly these contaminants can be removed with only a small temperature rise and the adsorbent has increased stability upon multiple regenerations. This adsorbent comprises a zeolite, alumina and a metal component (Madd) which is present in an amount of at least 10 mole % of the stoichiometric amount of metal (expressed as the oxide) needed to compensate for the negative charge of the zeolite lattice.

SUMMARY OF THE INVENTION

This invention relates to a solid shaped adsorbent, a process for preparing the adsorbent and a process for removing contaminants from a hydrocarbon stream using the adsorbent. Accordingly, one embodiment of the invention is a solid shaped adsorbent for purifying hydrocarbon streams comprising an alumina component, a zeolite component and a metal component selected from the group consisting of alkali metals, alkaline earth metals and mixtures thereof, the metal component present in an amount of at least 10 mole % of the stoichiometric amount of metal needed to compensate for the negative charge of the zeolite lattice, expressed as the oxide.

Another embodiment of the invention is a process for preparing a solid shaped adsorbent for purifying hydrocarbon streams comprising an alumina component, a zeolite component and a metal component selected from the group consisting of alkali metals, alkaline earth metals and mixtures thereof, the metal component present in an amount of at least 10 mole % of the stoichiometric amount of metal needed to compensate for the negative charge of the zeolite lattice, expressed as the oxide.

The process comprises forming a shaped article by combining an alumina component, a zeolite component and a metal component precursor in any order to form a shaped article, curing the shaped article at curing conditions to give a cured shaped article and activating the cured article at activation conditions to give the solid shaped adsorbent.

Yet another embodiment of the invention is a process for removing contaminants from hydrocarbon streams comprising contacting the stream with the solid shaped adsorbent described above at adsorption conditions to remove at least a portion of at least one contaminant.

These and other objects and embodiments will become clearer after a detailed description of the invention.

DETAILED DESCRIPTION OF THE INVENTION

Applicant's invention comprises a solid shaped adsorbent, a process for preparing the adsorbent and purification processes using the adsorbent. With regard to the solid shaped adsorbent, one necessary component is an activated alumina. Activated aluminas include aluminas having a surface area usually greater than 100 $m^2/g$ and typically in the range of 100 to 400 $m^2/g$. Further, the activated alumina powder is preferably obtained by rapid dehydration of aluminum hydroxides, e.g., alumina trihydrate of hydrargillite in a stream of hot gasses or solid heat carrier. Dehydration may be accomplished in any suitable apparatus using the stream of hot gases or solid heat carrier. Generally, the time for heating or contacting with the hot gases is a very short period of time, typically from a fraction of a second to 4 or 5 seconds. Normally, the temperature of the gases varies between 400° and 1000° C. The process is commonly referred to as flash calcination and is disclosed, for example in U.S. Pat. No. 2,915,365, incorporated herein by reference. However, other methods of calcination may be employed.

The activated aluminas suitable for use in the present invention have a median particle size in the range of 0.1 to 300 microns, preferably 1 to 100 microns and typically 1 to 20 microns. In certain instances, it may be desirable to use aluminas with a median particle size of 1 to 10 microns. The alumina may be ground to the desired particle size before or after activation. The activated alumina typically has an LOI (loss on ignition) in the range of about 5 to 12% at a temperature of 200° to 1000° C.

One source of activated alumina is gibbsite which is one form of alumina hydrate derived from bauxite using the Bayer process. However, alpha alumina monohydrate, pseudoboehmite or the alumina trihydrate may be used if sufficiently calcined. Other sources of alumina may also be utilized including clays and alumina alkoxides.

Another necessary component of the present invention is a zeolite. Zeolites are crystalline aluminosilicate compositions which are microporous and which have a three-dimensional oxide framework formed from corner sharing $AlO_2$ and $SiO_2$ tetrahedra. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. The zeolites which can be used in the present invention are those which have a pore opening of about 5 to about 10 Å.

In general, the zeolites have a composition represented by the empirical formula:

$$M_{2/n}O:Al_2O_3:bSiO_2$$

M is a cation having a valence of "n" and "b" has a value of about 2 to about 500. Preferred zeolites are those that have a $SiO_2/Al_2O_3$ ratio of about 2:1 to about 6:1 and/or those having the crystal structure of zeolite X, faujasite, zeolite Y, zeolite A, mordenite, beta and ferrierite. Especially preferred zeolites are zeolites X, Y and A.

Preparation of these zeolites is well known in the art and involves forming a reaction mixture composed of reactive sources of the components which mixture is then hydrothermally reacted to form the zeolite. Specifically, the synthesis of zeolite Y is described in U.S. Pat. Nos. 3,130,007 and 4,503,023 and that of zeolite X in U.S. Pat. Nos. 2,883,244 and 3,862,900 the disclosures of which are incorporated by reference.

Although the synthesis of zeolites, and zeolites X and Y in particular, are well known, a brief description will be presented here for completeness. Reactive sources of M include the halide and hydroxide compounds of alkali or alkaline earth metals such as sodium chloride, sodium hydroxide, potassium hydroxide, etc. Aluminum sources include but are not limited to boehmite alumina, gamma alumina and soluble aluminates such as sodium aluminate or tetraethylammonium aluminates. Finally, silicon sources include, silica, silica hydrosol, silicic acid, etc.

The reactive sources are combined into a reaction mixture which has a composition in terms of mole ratios of the oxides of:

| | |
|---|---|
| $SiO_2/Al_2O_3 =$ | 8 to 12 |
| $M_2O/Al_2O_3 =$ | 2.5 to 4 |
| $H_2O/M_2O =$ | 120 to 180 | and the mixture is then reacted to form the zeolite.

As synthesized, the zeolites will contain "M" metals in the channels and/or pores. The function of these metal cations is to balance the negative charge of the zeolite lattice. Since these cations are not part of the framework, they are exchangeable and are said to occupy exchange sites. The amount of metal cations present in the zeolite is referred to as the stoichiometric amount or the maximum ion exchange capacity of the zeolite. This amount is usually expressed in moles.

Since the metal cations initially present in the zeolite are exchangeable they can be exchanged for other (different) alkali metals, alkaline earth metals, hydronium ions, ammonium ions or mixtures thereof. If the zeolite to be used contains partially or completely hydronium or ammonium ions, then these ions must be fully exchanged with alkali metals, alkaline earth metals or mixtures thereof, either before or during the preparation of the composite adsorbent.

Another necessary component of the shaped adsorbent of this invention is a metal component (Madd) selected from the group consisting of alkali, alkaline earth metals and mixtures thereof. This metal component (Madd) is in addition to the metal cation (M) present in the exchange sites of the zeolite. Additionally the Madd metal can be the same or different than the M metal. For example, the M metal in a zeolite can be potassium whereas the Madd can be sodium.

Specific examples of Madd include but are not limited to sodium, potassium, lithium, rubidium, cesium, calcium, strontium, magnesium, barium, zinc and copper. The source of the (metal component precursor) can be any compound which at activation conditions, (see infra) decomposes to the metal oxide. Examples of these sources are the nitrates, hydroxides, carboxylates, carbonates and oxides of the metals. The shaped adsorbent can be prepared by combining the three components in any order and forming into a shaped article although not necessarily with equivalent results.

In one method, the alumina, zeolite and an aqueous solution of the desired metal compound are mixed and formed into a shaped article. For example, gamma alumina, zeolite X and a solution of sodium acetate can be combined into a dough and then extruded or formed into shapes such as pellets, pills, tablets or spheres (e.g. by the oil drop method) by means well known in the art. A preferred method of forming substantially rounded shapes or bodies involves the use of a pan nodulizer. This technique uses a rotating pan or pan nodulizer onto which is fed the alumina component, zeolite component and a solution of the metal component thereby forming substantially rounded articles or bodies.

Another method of forming the shaped article is to mix powders of the alumina, zeolite and metal compound followed by formation of pellets, pills, etc. A third method is to combine the alumina and zeolite components (powders), form them into a shaped article and then impregnate the shaped article with an aqueous solution of the metal compound. The forming step is carried out by any of the means enumerated above.

In preparing a solution of the desired metal compound, it is preferred to adjust the pH to a value from about 7 to about 14, more preferably from about 12 to about 14 and most preferably from about 12.7 to about 13.8. The pH of the solution is controlled by adding the appropriate amount of the desired metal hydroxide. For example, if sodium is the desired metal, sodium acetate can be used to form the aqueous solution and the pH is then adjusted using sodium hydroxide.

Having obtained the shaped articles, they are cured or dried at ambient temperature up to about 200° C. for a time of about 5 minutes to about 25 hours. The shaped articles can be cured in batches e.g. bins or trays or in a continuous process using a moving belt. Once the shaped articles are cured, they are activated by heating the cured articles at a temperature of about 275° C. to about 600° C. for a time of about 5 to about 70 minutes. The heating can be done with the articles in a moving pan or in a moving belt where the articles are direct fired to provide the finished solid adsorbent.

The relative amount of the three components can vary considerably over a wide range. Usually the amount of alumina varies from about 40 to about 90% of the adsorbent and the amount of zeolite varies from about 5 to about 55 wt. % of the adsorbent. The amount of metal component, Madd, can also vary considerably, but must be present in an amount equal to at least 10% of the stoichiometric amount of the metal cation, M, present in the exchange sites of the zeolite. For practical reasons, the maximum amount of Madd should be no more than 50% of the stoichiometric amount of M. In absolute terms, it is preferred that the amount of Madd be present from about 0.015 to about 0.08 moles of Madd per 100 gm of adsorbent. The amounts of M and Madd are reported or expressed as the oxide of the metal, e.g. $Na_2O$.

The finished adsorbent can now be used to remove contaminants from various hydrocarbon streams. The streams which can be treated include but are not limited to hydrocarbon streams, especially those containing saturated and/or unsaturated hydrocarbons. Olefin stream such as ethylene, propylene and butylenes can be especially treated using the instant adsorbent. These streams will contain one or more of the following contaminants: $H_2O$, $CO$, $O_2$, $CO_2$, $COS$, $H_2S$, $NH_3$, $AsH_3$, $PH_3$, Hg, methanol, mercaptans and other S- or O-containing organic compounds.

The hydrocarbon streams are purified by contacting the stream with the solid adsorbent at adsorption conditions. The contacting can be carried out in a batch or continuous process with continuous being preferred. The adsorbent can be present as a fixed bed, moving bed or radial flow bed with fixed bed being preferred. When a fixed bed is used, the feed stream can be flowed in an upflow or downflow direction, with upflow being generally preferred for liquid feeds. If a moving bed is used the feed stream flow can be either co-current or counter-current. Further, when a fixed bed is used, multiple beds can be used and can be placed in one or more reactor vessel. Adsorption conditions include a temperature of about ambient to about 80° C., a pressure of about atmospheric to about 100 atm. ($1.01 \times 10^4$ kPa) and a contact time which depends on whether the hydrocarbon stream is a liquid or gaseous stream. For a liquid stream the contact time expressed in terms of liquid hourly space velocity (LHSV) is from about 0.5 to about 10 $hr^{-1}$, while for a gaseous stream, the gas hourly space velocity varies from about 500 to about 10,000 $hr^{-1}$.

After a certain amount of time, which time depends on the concentration of contaminants, the size of the bed and the space velocity, the adsorbent will be substantially spent, i.e. has adsorbed an amount of contaminant(s) such that the level of contaminant in the purified stream is above an acceptable level. At this time, the adsorbent is removed and replaced with fresh adsorbent. The spent adsorbent can be regenerated by means well known in the art and then placed back on service. In a typical regeneration procedure, the adsorbent is first drained and depressurized followed by a cold purge with an inert stream. Next, a warm purge in a downflow direction at 80–150° C. removes the retained hydrocarbons from the bed. Finally, the temperature is slowly raised to 280–320° C. and held there for at least 2 hours and then cooled to ambient temperature.

The following examples are set for in order to more fully illustrate the invention. It is to be understood that the examples are only by way of illustration and are not intended as an undue limitation on the broad scope of the invention as set forth in the appended claims.

EXAMPLE 1

Balls containing alumina, zeolite 13X and sodium where prepared as follows. A rotating pan device was used to continuously form beads by simultaneously adding activated alumina powder (AP) and zeolite 13X powder (Z) while spraying the powders with a sodium acetate solution (NaAc). The mass ratio (on a volatile free basis) was 1.0 AP:0.23 Z:0.04 NaAc. Water was added as needed to keep the sodium acetate dissolved and to provide for sufficient agglomeration. The pH of the NaAc solution was adjusted to 13.3 by adding a NaOH solution. The balls, which had a size distribution from 1.2 to 4 mm were cured at 60–80° C. for three hours using a heated belt. Finally, the cured beads were activated in an oven at about 450° C. for one hour. The amount of each component (wt. %) on a volatile free basis was found to be 78.7% AP; 18.1% Z; 3.2% $Na_2O$.

EXAMPLE 2

The procedure set forth in Example 1 was used to prepare balls except that the mass ratio of AP:Z:NaAc was 1.0:0.55:0.035. The amount of each component (wt. %) on a volatile free basis was found to be 63.1% AP; 34.7% Z; 2.2% $Na_2O$.

EXAMPLE 3

The procedure set forth in Example 1 was used to prepare balls except the mass ratio of AP:Z:NaAc was 1.0:0.37:0.05. The amount of each component (wt. %) on a volatile free basis was found to be 70.4% AP; 26.1% Z; 3.5% $Na_2O$.

EXAMPLE 4

The procedure in Example 3 was used to prepare balls except that water was used instead of NaAc. The amount of each component (wt. %) on a volatile free basis was found to be 72.9% AP; 26.9% Z; 0.2% $Na_2O$.

EXAMPLE 5

The process of Example 1 was carried out except that zeolite NaY (obtained from UOP LLC) was used instead of zeolite 13 X and the ratio was 1AP : 0.37Z. The amount of each component (wt. %) on a volatile free basis was found to be 72.9% AP; 26.9% Z; 0.2% $Na_2O$.

EXAMPLE 6

In a rotating container there were placed 500g of the balls from Example 5 and 200g of a 4.6 wt. % sodium acetate solution. The balls were cured by rotating the closed container for one hour and then activated as per Example 1. The amount of each component (wt. %) on a volatile free basis was found to be 72.36% AP; 26.7% Z; 0.94% $Na_2O$.

EXAMPLE 7

Balls were prepared as in Example 6 except that a solution containing 10.9 wt. % sodium acetate was used. The amount of each component (wt. %) on a volatile free basis was found to be 71.65% AP; 26.44 Z; 1.91% $Na_2O$.

EXAMPLE 8

Balls were prepared as in Example 6 except that a solution containing 17.1% sodium acetate was used. The amount of each component (wt. %) on a volatile free basis was found to be 70.9% AP; 26.18% Z; 2.88% $Na_2O$.

EXAMPLE 9

Samples from Examples 1–7 were tested for $CO_2$ and propylene adsorption using a McBain balance. $CO_2$ is used to measure adsorption of acidic gases, while propylene measures the ability to adsorb organic compounds. About 30mg of each sample was heated in flowing helium to 400° C. at a rate of 25° C./min. held there for about 45 min. and then cooled (under helium to room temperature). Adsorption was carried out by flowing a stream of either 1% propylene in helium or 1.5% $CO_2$ in helium over the sample at 38° C. for 20 minutes and measuring the weight change. The results are presented in Table 1

TABLE 1

Adsorption Capacity* of Various Adsorbents

| Sample ID | $Na_2O$ mol/100/gm total | $Na_2O$ mol/100 gm added | Propylene | $CO_2$ |
|---|---|---|---|---|
| Example 1 | 0.108 | 0.052 | 2.57 | 3.9 |
| Example 2 | 0.147 | 0.035 | 4.06 | 4.8 |
| Example 3 | 0.140 | 0.056 | 3.22 | 4.3 |
| Example 4 | 0.089 | 0.003*** | 3.3 | 3.5 |
| Example 5 | 0.058 | none | 2.37 | 0.78** |
| Example 6 | 0.071 | 0.012 | 2.29 | 0.85** |
| Example 7 | 0.087 | 0.028 | 2.2 | 0.99** |
| Example 8 | 0.103 | 0.044 | 2.22 | 1.1* |

*Capacity in g adsorbate/100 g adsorbent
**pre-treatment temperature 232° C.
***added as NaOH to adjust the pH during preparation Examples 1–4 used zeolite X while Examples 5–8 used zeolite Y. For both zeolites it is observed that the propylene adsorption is affected very little by the addition of sodium, but the $CO_2$ adsorption improves considerably.

EXAMPLE 10

Samples from Examples 1–4 were tested for surface reactivity using 1-hexene as the probe molecule. About 70mg from each sample (as a powder) was placed in a tubular flow reactor placed in a furnace. Each sample was activated at 350° C. for 1 hour in helium and then cooled to 150° C. Next a feed stream prepared by bubbling helium through a saturator containing 1-hexene was flowed through the catalyst at a rate of 20cc/min, while measuring the hexene conversion at various temperatures in the temperature range of 150° C. to 500° C. Hexene conversion was measured using a gas chromatograph. The major product of this reaction at low conversion were 2-hexene and 3-hexene. Formation of methyl branched isomers and cracking products occurred at high conversion. The overall conversion of 1-hexene are shown in Table 2.

TABLE 2

1-hexene Conversion (%) of Various Adsorbents

| Sample ID | 200° C. | 250° C. | 350° C. |
|---|---|---|---|
| Example 1 | 0 | 0 | 7.4 |
| Example 2 | 0 | 0 | 15.5 |
| Example 3 | 0 | 0 | 7.5 |
| Example 4 | 18.8 | 57.8 | 83.4 |

This data clearly shows that an alumina/zeolite adsorbent without additional sodium (Example 4) has much more reactivity for 1-hexene conversion. Since the adsorbents are regenerated in the same temperature range as the range in Table 2, the low catalytic activity of the adsorbents of Examples 1–3 indicates that the presence of sodium (at the above levels) would strongly reduce the likelihood of coking or run-away reaction when the above adsorbents undergo regeneration.

Samples from Example 5–8 were tested as above and the results are presented in Table 3.

TABLE 3

1-hexene Conversion (%) of Various Adsorbents

| Sample ID | 200° C. | 250° C. | 300° C. |
|---|---|---|---|
| Example 5 | 45.2 | 79.4 | 89 |
| Example 6 | 5.9 | 38.5 | 71.3 |
| Example 7 | 0.7 | 6.4 | 24.5 |
| Example 8 | 0.2 | — | 10.8 |

The results in Table 3 show the same performance using zeolite Y as shown in Table 2 using zeolite X. That is the presence of additional sodium greatly reduces the reactivity of the adsorbent.

EXAMPLE 11

A series of zeolites were combined with alumina (AP) and sodium acetate powders and thoroughly mixed. A small sample was transferred to a microbalance, activated in a helium flow at 700° C. and then cooled to 38° C. Propylene adsorption measurements were carried out as per Example 9 and the results presented in Table 4.

TABLE 4

Effect of Components of Propylene Adsorption

| Sample ID | Composition (wt. %) | | | | | Propylene Adsorption (g/100 g) |
|---|---|---|---|---|---|---|
| | AP | NaY | 13X | 3A | $Na_2O$ | |
| A | 72.7 | 27.3 | | | | 3.29 |
| B | 69.7 | 26.2 | | | 4.1 | 2.66 |
| C | | | 25.4 | 70.6 | 4.0 | 1.33 |
| D | 77.1 | 22.9 | | | | 2.42 |
| E | 74.7 | 22.2 | | | 3.2 | 2.12 |
| F | | 21.2 | | 74.6 | 4.2 | 0.84 |

The results in Table 4 show that the addition of sodium does not affect propylene adsorption very much (compare samples A vs. B and D vs. E). However, when the adsorbent contains only zeolites, additional sodium lowers propylene adsorption (samples A vs. C and D vs. F). This shows the function of the alumina.

What is claimed is:

1. A solid shaped adsorbent for purifying hydrocarbon streams comprising an alumina component, a zeolite component and a metal component (Madd), the metal component present in an amount from about 0.015 to 0.08 moles of the metal as the oxide per 100 g of adsorbent and where the alumina is present in an amount from about 40 to about 90 wt. % of the adsorbent.

2. The adsorbent of claim 1 where the zeolite is selected from the group consisting of zeolite X, zeolite Y, zeolite A and mixtures thereof.

3. The adsorbent of claim 2 where the zeolite is zeolite X.

4. The adsorbent of claim 1 where the metal component (Madd) is an alkali metal selected from the group consisting of sodium, potassium, lithium, rubidium, cesium and mixtures thereof.

5. The adsorbent of claim 4 where the metal component is sodium.

6. The adsorbent of claim 1 where the zeolite is present in an amount from about 5 to about 55 wt. % of the adsorbent.

7. A process for preparing a solid shaped adsorbent for purifying hydrocarbon streams comprising an alumina component, a zeolite component and a metal component (Madd) selected from the group consisting of sodium, potassium, lithium, rubidium, cesium and mixtures thereof the metal component present in an amount from about 0.015 to about 0.08 moles of metal as the oxide per 100 g of adsorbent and where the alumina is present in an amount from about 40 to about 90 wt. % of the adsorbent; the process comprising forming a shaped article by combining an alumina component, a zeolite component and a metal component precursor in any order to form a shaped article, curing the shaped article at curing conditions to give a cured shaped article and activating the cured article at activation conditions to give the solid shaped adsorbent.

8. The process of claim 7 where the zeolite component is selected from the group consisting of zeolite X, zeolite Y, zeolite A and mixtures thereof.

9. The process of claim 7 where the metal component precursor is selected from the carboxylate, carbonate and hydroxide compound of the metal component.

10. The process of claim 9 where the carboxylate is an acetate compound of the metal component.

11. The process of claim 7 where the shaped article is selected from the group consisting of extrudes, pills, tablets, spheres and irregular shaped particles.

12. The process of claim 7 where the curing conditions include a temperature of about ambient to about 200° C. and a time of about 5 minutes to about 25 hours.

13. The process of claim 7 where the activation conditions include a temperature of about 275° C. to about 600° C. and a time of about 5 to about 70 minutes.

14. The process of claim 7 where the alumina, zeolite and an aqueous solution of the metal precursor are mixed and formed into a shaped article.

15. The process of claim 7 where the alumina and zeolite components are formed into a shaped article and then contacted with an aqueous solution containing a metal precursor.

16. The process of claim 7 where alumina powder, zeolite powder and metal precursor powder are combined and formed into a shaped article.

* * * * *